(12) United States Patent
D'Hiver

(10) Patent No.: US 9,827,354 B2
(45) Date of Patent: Nov. 28, 2017

(54) DETECTION/STIMULATION IMPLANTABLE MICROLEAD INCORPORATING AN ANTI-INFLAMMATORY AGENT

(71) Applicant: SORIN CRM SAS, Clamart (FR)

(72) Inventor: Philippe D'Hiver, Chatillon (FR)

(73) Assignee: SORIN CRM S.A.S., Clamart (FR)

( * ) Notice: Subject to any disclaimer, the term of this patent is extended or adjusted under 35 U.S.C. 154(b) by 538 days.

(21) Appl. No.: 14/299,243

(22) Filed: Jun. 9, 2014

(65) Prior Publication Data
US 2014/0364793 A1    Dec. 11, 2014

(30) Foreign Application Priority Data
Jun. 11, 2013  (FR) ..................... 13 55385

(51) Int. Cl.
*A61L 31/16*    (2006.01)
*A61N 1/05*    (2006.01)

(52) U.S. Cl.
CPC ............... *A61L 31/16* (2013.01); *A61N 1/05* (2013.01); *A61N 1/0568* (2013.01); *A61N 2001/0585* (2013.01)

(58) Field of Classification Search
CPC ...... A61B 18/1477; A61B 2018/00577; A61B 2218/002; A61B 2018/1497; A61B 2018/00744; A61N 1/0568; A61N 1/0551; A61N 1/0575; A61N 1/0587; A61N 1/36082; A61N 1/36117; A61N 1/056; A61N 1/05; A61N 1/0563; A61N 1/36017;
(Continued)

(56) References Cited

U.S. PATENT DOCUMENTS 3,366,728 A * 1/1968 Garwin et al. ............ 174/113 R
4,506,680 A * 3/1985 Stokes ................. A61N 1/0565
424/424
(Continued)

FOREIGN PATENT DOCUMENTS

| EP | 2 581 107 A1 | 4/2013 |
| WO | WO-01/23034 A1 | 4/2001 |
| WO | WO-2008/013908 A1 | 1/2008 |

OTHER PUBLICATIONS

Wigal. "Purifying Acetanilide by Recrystallization." Modular Laboratory Program in Chemistry. 2004. Accessed online: <http://www.chm.uri.edu/bdeboef/chm292/rextallization.pdf>.*
(Continued)

*Primary Examiner* — Scott Medway
(74) *Attorney, Agent, or Firm* — Foley & Lardner LLP

(57) ABSTRACT

A microlead includes a conductive cable formed by a strand of microcables, each microcable being formed of a strand of individual metallic wires. The microlead also includes an insulation layer sheathing the cable. The microlead further includes at least one exposed area formed in the insulation layer so as to form a corresponding electrode of the microlead. The microlead further includes a pharmacologically active agent (e.g., an anti-inflammatory agent) configured to gradually be released into the environment of the microlead after implantation of the microlead. The pharmacologically active agent may be a soluble material. An interstitial space, delimited by the inner wall of the insulation layer and existing in the remainder between the wires of each microcable, is filled with the pharmacologically active agent.

20 Claims, 3 Drawing Sheets

(58) Field of Classification Search
CPC ........ A61N 1/3752; A61M 2025/0057; A61M 25/007; A61M 37/0069; A61F 2250/0068
See application file for complete search history.

(56) References Cited

U.S. PATENT DOCUMENTS

| | | | |
|---|---|---|---|
| 4,646,428 A * | 3/1987 | Marancik et al. | 29/599 |
| 4,690,155 A * | 9/1987 | Hess | 607/122 |
| 4,972,848 A * | 11/1990 | Di Domenico et al. | 607/127 |
| 5,100,388 A * | 3/1992 | Behl et al. | 604/113 |
| 5,246,014 A * | 9/1993 | Williams et al. | 607/122 |
| 5,380,307 A * | 1/1995 | Chee et al. | 604/264 |
| 5,385,579 A * | 1/1995 | Helland | 607/130 |
| 5,496,360 A | 3/1996 | Hoffmann et al. | |
| 5,520,682 A * | 5/1996 | Baust et al. | 606/24 |
| 5,760,341 A * | 6/1998 | Laske et al. | 174/126.2 |
| 5,766,192 A * | 6/1998 | Zacca | 606/159 |
| 5,766,527 A * | 6/1998 | Schildgen | A61N 1/056 264/104 |
| 5,792,105 A * | 8/1998 | Lin et al. | 604/103.01 |
| 5,796,044 A * | 8/1998 | Cobian et al. | 174/103 |
| 5,861,023 A * | 1/1999 | Vachon | A61N 1/0563 607/121 |
| 6,235,019 B1 * | 5/2001 | Lehmann et al. | 606/22 |
| 6,240,321 B1 * | 5/2001 | Janke et al. | 607/122 |
| 6,295,476 B1 * | 9/2001 | Schaenzer | 607/122 |
| 6,304,786 B1 * | 10/2001 | Heil, Jr. | A61N 1/0568 607/120 |
| 6,921,295 B2 * | 7/2005 | Sommer et al. | 439/668 |
| 7,047,082 B1 * | 5/2006 | Schrom | A61N 1/0551 607/116 |
| 7,065,411 B2 * | 6/2006 | Verness | 607/116 |
| 7,184,839 B2 * | 2/2007 | Clemens et al. | 607/120 |
| 7,501,579 B2 * | 3/2009 | Michael et al. | 174/126.1 |
| 8,066,702 B2 * | 11/2011 | Rittman et al. | 606/41 |
| 9,320,890 B2 * | 4/2016 | Cleek | A61L 29/085 |
| 9,560,979 B2 * | 2/2017 | Shan | A61N 1/056 |
| 2002/0062122 A1 * | 5/2002 | Lehmann et al. | 606/23 |
| 2002/0077685 A1 * | 6/2002 | Sundquist et al. | 607/116 |
| 2003/0204233 A1 * | 10/2003 | Laske et al. | 607/127 |
| 2004/0064158 A1 * | 4/2004 | Klein et al. | 607/9 |
| 2004/0167209 A1 * | 8/2004 | Dancer et al. | 514/469 |
| 2004/0199104 A1 * | 10/2004 | Ujhelyi | A61M 5/14276 604/65 |
| 2005/0027340 A1 * | 2/2005 | Schrom et al. | 607/116 |
| 2005/0267458 A1 * | 12/2005 | Paul et al. | 606/41 |
| 2006/0106443 A1 * | 5/2006 | Michael | A61N 1/056 607/122 |
| 2006/0198866 A1 * | 9/2006 | Chang | A61L 27/34 424/423 |
| 2006/0217655 A1 * | 9/2006 | Vitullo et al. | 604/21 |
| 2007/0051531 A1 * | 3/2007 | Borgaonkar | A61N 1/0568 174/126.1 |
| 2008/0033520 A1 * | 2/2008 | Jolly | A61N 1/0541 607/137 |
| 2008/0058758 A1 * | 3/2008 | Ranchod et al. | 604/508 |
| 2009/0076588 A1 * | 3/2009 | Weber | A61F 2/90 623/1.15 |
| 2009/0099612 A1 * | 4/2009 | Armstrong | A61L 31/10 607/3 |
| 2010/0121422 A1 * | 5/2010 | Jolly | A61K 9/0019 607/137 |
| 2010/0137928 A1 * | 6/2010 | Duncan et al. | 607/5 |
| 2010/0211147 A1 * | 8/2010 | Schiefer | A61N 1/05 607/116 |
| 2011/0087317 A1 * | 4/2011 | Borgaonkar | A61N 1/05 607/120 |
| 2011/0137382 A1 * | 6/2011 | Swanson | 607/72 |
| 2011/0282343 A1 * | 11/2011 | Kunis | 606/41 |
| 2011/0288388 A1 * | 11/2011 | Shah et al. | 600/347 |
| 2013/0166007 A1 * | 6/2013 | True et al. | 607/116 |
| 2014/0107456 A1 * | 4/2014 | Regnier | A61N 1/056 600/381 |
| 2014/0213971 A1 * | 7/2014 | Dolan et al. | 604/104 |
| 2014/0358160 A1 * | 12/2014 | Regnier et al. | 606/129 |

OTHER PUBLICATIONS

Search Report for French Patent Application No. FA 781975 FR 1355385, dated Oct. 4, 2013, 2 pages.

* cited by examiner

DETECTION/STIMULATION IMPLANTABLE MICROLEAD INCORPORATING AN ANTI-INFLAMMATORY AGENT

CROSS-REFERENCE TO RELATED APPLICATION

This application claims the benefit of and priority to French Patent Application No. 1355385, filed Jun. 11, 2013. French Patent Application No. 1355385 is hereby incorporated by reference in its entirety.

BACKGROUND

The invention relates to "active implantable medical devices" as defined by Directive 90/385/EEC of 20 Jun. 1990 of the Council of the European Communities. The invention may relate to implantable devices for continuous monitoring of the heart rhythm and delivery of electrical stimulation or resynchronization pulses, if necessary, to the heart. Embodiments of the invention may relate, more specifically, to pacemaker leads to be implanted in the cardiac coronary network to allow stimulation of a left, ventricular or atrial cavity.

A trend in recent developments in left ventricle pacing lead is the reduction of the diameter of the implantable part in the coronary network. The size of the lead body is indeed a factor directly related to the controlled guiding capacity of the lead in the venous coronary network, to be able to select specific stimulation sites located in certain collateral veins.

EP 2581107 A1 (Sorin CRM SAS) describes a lead composed in its active distal part by a microcable having a diameter of the order of 0.5 to 2 French (0.17 to 0.66 mm). This microcable includes an electrically conductive core cable formed by one or more strands of a plurality of composite strands. The microcable has a polymer insulation layer partially surrounding the core cable. The isolation layer is punctually exposed so as to expose the microcable in one or more points constituting a network of electrodes connected in series. The free end of the strand is also provided with a reported distal electrode.

The very small diameter of the microcable allows exploiting the entire length of the vein and cannulation of veins of very small diameter. These portions of the coronary network have generally not been exploited until now due to the excessive size of conventional coronary leads. It thus becomes possible to treat areas difficult to reach, and thereby make optimal use of all the veins present in the basal area. One benefit is a reduced risk of phrenic nerve stimulation; such risk generally increases when the lead is too distal. With such a microlead, it is even possible to cross anastomosis (passages present from the end of certain veins to another vein) with the possibility of advancing the microlead in a first vein ("go" vein) followed by an anastomosis into a second vein ("return" vein) going back thereof. This allows for stimulation of the left ventricle from two distinct and remote regions.

Moreover, the multiplication of stimulation points in a deep zone of the coronary network allows (unlike traditional leads) simultaneous stimulation of multiple zones of the epicardium in the region of stimulation, thereby improving the chances of myocardium optimal resynchronization. Finally, the structure of this microlead gives it great strength that improves its long-term biostability.

Another set of issues relates to the biological phenomenon of inflammation of tissue that is in mechanical contact with the lead. This contact exerts a pressure and is sometimes accompanied by small movements. These mechanical actions result in tissue inflammation, over the course of a few weeks. This is also a phenomenon encountered with all types of leads, whether they are placed in the coronary veins or in the cardiac chambers. In terms of device operation, this inflammation requires increased energy of delivered pulses due to the increase in the stimulation threshold (capture threshold). This also makes reassessment at regular intervals of the capture threshold necessary, so as to adapt the level of the energy delivered to the variations of this threshold according to the degree of inflammation. In summary, inflammation induces energy consumption of the device, and a risk of loss of capture.

The conventional technique to reduce this inflammation phenomenon is to incorporate to the leads molded silicone parts loaded of an anti-inflammatory agent. The anti-inflammatory agent is generally a steroid, e.g. a glucocorticoid such as dexamethasone sodium phosphate (DSP hereinafter). These molded parts are arranged in particular at the electrodes, to mitigate the effects of inflammation on the elevation of the capture threshold. The anti-inflammatory agent is gradually released by diffusion into and out of the silicon after implantation of the lead.

U.S. Pat. No. 5,496,360 A is an example of a lead designed according to this technique, with a hollow end electrode including an internal chamber. The internal chamber includes a polymer matrix impregnated with an agent such as the DSP. The chamber communicates with the outside through a narrow axial channel for the DSP to diffuse slowly around the electrode by effect of "osmotic pump" with the surrounding fluids. However, this technique is complex and expensive to implement because of the multiple process steps it involves: screening of the steroid to control the grain size, mixture preparation of silicone paste and steroid, molding and trimming, visual inspection of molded parts, and manual integration, lead by lead, of the silicone parts containing steroid. Further, this technique is in practice difficult to envisage for a microlead of a diameter less than 0.5 mm. The extremely fine size of such a microlead makes inadequate the implementation of reported silicone parts loaded with a steroid, or the machining of hollow parts as disclosed in the U.S. Pat. No. 5,496,360 A cited above.

SUMMARY

In some microleads, the strands of microcables forming the core cable of the microlead actually occupies a portion of the internal volume available under the isolation layer (e.g., in practice about half of this volume). One feature of the invention is to use this space to incorporate a pharmacologically active agent, especially an anti-inflammatory agent, which will be gradually released into the environment at the electrodes. The electrodes are specifically comprised of exposed areas in the insulation layer, which thereby allow communication between the interior volume of the microlead and the external environment.

More specifically, the invention relates to a lead having an active distal portion devoid of central lumen and formed by: an electrically conductive cable formed by a strand of microcables, each microcable being formed of a strand of single wires; an insulation layer of an electrically insulating material sheathing the cable; at least one exposed area formed in the insulation layer so as to form a corresponding electrode of the microlead; and a pharmacologically active agent to be gradually released into the environment of the microlead after implantation thereof.

In certain embodiments, the pharmacologically active agent is present as a soluble material. The interstitial space, delimited by the inner wall of the insulation layer, remaining between the strands of each microcable, is filed by the pharmacologically active agent. The pharmacologically active agent may be, in particular, an anti-inflammatory agent, particularly a glucocorticoid such as dexamethasone sodium phosphate or a non-steroidal anti-inflammatory agent.

In a preferred embodiment, the distal end of the microlead includes an extension of the insulation layer beyond the termination of said cable. This extension defines an empty space forming an additional reservoir for the pharmacologically active agent, the reservoir being closed at its distal end by an atraumatic element.

The invention also relates to a method adapted for the manufacture of a lead as above. This method may include the following steps: a) obtaining a microlead having an active distal portion formed by an electrically conductive cable formed by a strand of micro-cables each of which is formed of a strand of individual metal wires, an insulation layer of electrically insulating material sheathing the cable, and at least one exposed zone formed in the insulation layer so as to form a corresponding electrode of the microlead; b) immersing the microlead in a bath of a pharmacologically active agent solution; c) placing the microlead and the bath in a sealed chamber and evacuating the chamber, so as to evacuate the air remaining in the interstitial space defined by the inner wall of the insulation layer, and remaining between the wires of each microcable of the microlead; d) recovery of pressure, or implementation of overpressure in the enclosure, so as to induce the penetration of the pharmacologically active agent in said interstitial space; and e) extracting the microlead from the bath and drying the microlead, so as to extract the liquid phase of the solution contained in the interstitial space.

Steps c) and d) can be repeated in sequence a plurality of times. Advantageously, the method further comprises a final step of: f) sterilization of the microlead obtained after step e) by passage through a chamber filled with ethylene oxide.

The pharmacologically active agent can in particular be dexamethasone sodium phosphate, the solution being an aqueous solution at a concentration between 0.3 and 5.0 g of dexamethasone for 100 ml of deionized water.

In yet another embodiment, the invention provides a method for providing a pharmacologically active agent to a stimulation area in the venous, arterial or lymphatic network. The method includes providing a microlead, the microlead comprising: an active distal portion formed by an electrically conductive cable formed by a strand of microcables, each microcable formed of a strand of individual metallic wires; an insulation layer of an electrically insulating material sheathing the cable; at least one exposed area formed in the insulation layer so as to form a corresponding electrode of the microlead; and an interstitial space defined by the internal wall of the insulation layer and between the wires of each microcable. The method further includes introducing a pharmacologically active agent to the interstitial space. Finally, the method includes implanting the microlead in the venous, arterial, or lymphatic network and allowing the pharmacologically active agent to diffuse through the at least one exposed area into the tissue surrounding the exposed area at the stimulation area.

DETAILED DESCRIPTION

Figure 1:
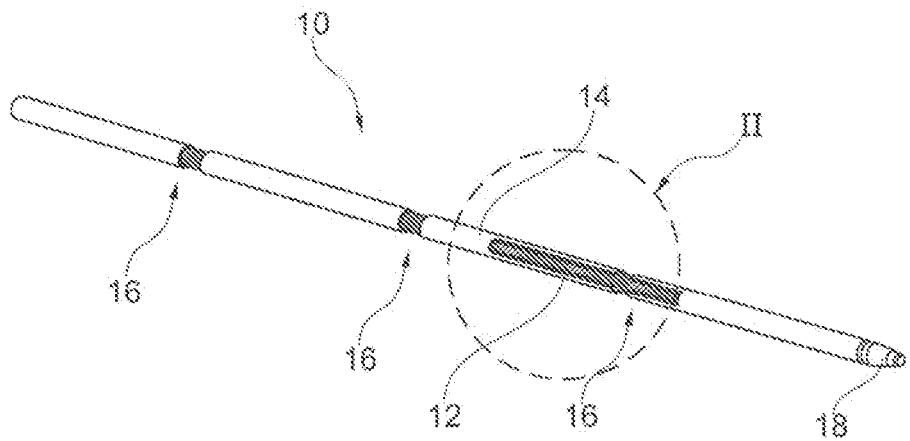
FIG. 1 shows the active distal end, in partial cutaway view, of a microlead implementing the teachings of the invention.
Figure 2:
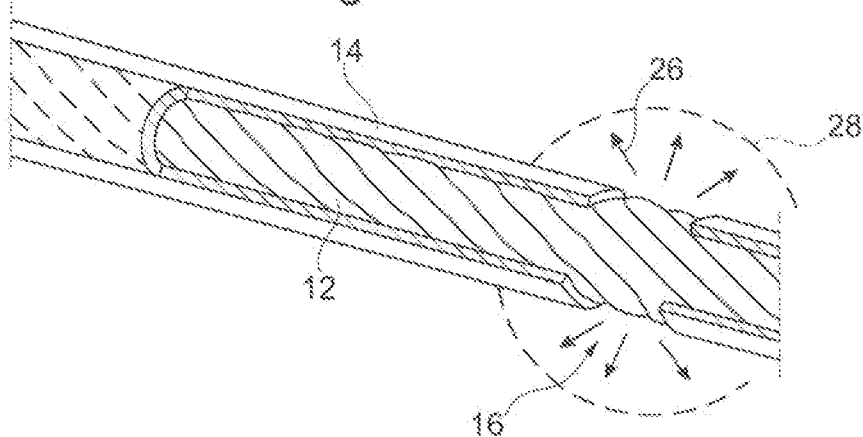
FIG. 2 is an enlarged detail of the spotted zone II of FIG. 1.

In FIGS. 1 and 2, the distal end 10 of a microlead for implantation, for example in the coronary system, is shown. This microlead includes, in its distal, active, end portion a core cable 12 sheathed by an insulation layer 14 of an electrically insulating material, preferably a material of high chemical resistance such as PTFE or ETFE.

Locally exposed areas 16 are formed in the insulation layer 14, to expose the conductor core cable 12 and thereby form a corresponding electrode of the lead. These zones 16 are for example exposed by laser ablation of the insulation layer 14. One end electrode or "tip" 18 may also be provided. The set of elements 16 and 18 correspond to a series of electrodes connected together in parallel for the collection of electric potentials and the delivery of stimulation pulses. This allows an increased number of opportunities for contact of the microlead with tissues and thus ensures multizone dissemination of the stimulation energy at several points of the left ventricle.

Figure 3:
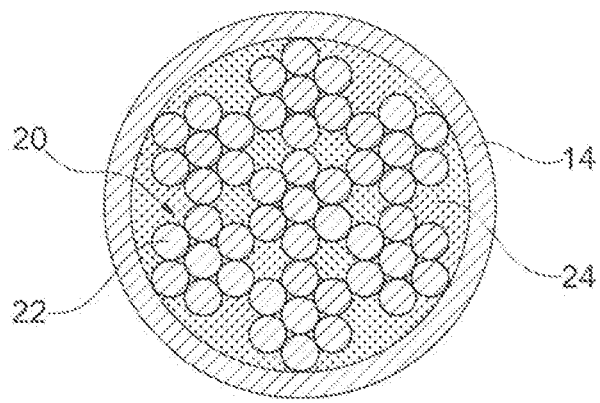
FIG. 3 is a cross section view, greatly enlarged, of the microlead of FIGS. 1 and 2.

FIG. 3 shows, more precisely, the internal structure of the microlead, in the insulating layer 14. The core cable 12 comprises a twisted multifilar structure of a plurality of microcables 20 stranded together (the stranding can be seen for example in the detail of FIG. 2). In the illustrated example, the core cable includes seven microcables 20. Each microcable 20 is itself formed by a strand of several individual unitary wires 22. In the illustrated example, each microcable 20 comprises seven wires 22, with a central wire surrounded by six peripheral wires. As such, in an exemplary embodiment, the core cable 12 includes a total assembly of 7×7=49 wires. This configuration is however not limiting, the core cable being possibly made of a number of wires typically between 15 and 300 strands, themselves grouped into a variable number of strands forming the microcables 20

Various structures of this type, in particular, are described in detail in the aforementioned EP 2581107 A1, which we can refer for further details, including the choice of materials and the method for assembling together the different wires.

The core cable 12 is shown to include microcables 20 and/or composite wires combining a structuring material with a high intrinsic fatigue resistance (stainless steel, alloy of the MP35NLT type, cobalt alloy, titanium, NiTi, etc.) and a radiopaque material (Ta, W, Ir, Pt, Au and their alloys). These different wires may be available, for example, from Fort Wayne Metals Company Inc., Fort Wayne, USA.

The microcable 12 is coated with a thin insulation layer 14. In certain embodiments, the insulation layer 14 is around 25 μm thick. The preferred characteristics for this layer are: fatigue resistance; electrical insulation; long-term biocompatibility; biostability; and the possibility of transformation and implementation compatible with the conductor of the core cable. To achieve this insulation layer, materials with high chemical inertness, as fluoropolymers, which also have very good insulation, will be preferred. Among these compounds, mention may be made especially of ETFE (ethylene tetrafluoroethylene). The methods for producing the insulation layer of core cable are, for example, co-extrusion on the conductor or the heating of a heat shrinkable tube. The exposed areas 16 are formed for example by plasma ablation or laser ablation of the ETFE layer.

The overall outside diameter of the microlead in its distal portion is smaller than 0.5 mm, for example an outer diameter of 0.35 mm. The unit diameter of the wires is generally between 20 and 40 μm, and the thickness of the insulation layer is, for example, 25 μm of ETFE.

The invention advantageously utilizes the presence of a residual volume comprising various crevices that exist between the microcables 20 of the strand, and between these microcables 20 and the inner wall of the insulation layer 14. The corresponding interstitial space 24 is physically a not-closed hollow volume, as it is capable of communicating with the outside at the location of the exposed zones 16. In the illustrated example, with a core cable comprising a double stranding of 7×7=49 wires and with the indicated dimensions of the outer diameter and of the insulation thickness, this interstitial space 24 can reach about 50% of the volume delimited by the inner wall of the insulation layer 14, or in this example a volume of 42.7 mm$^3$ for a length of 1 m for the distal portion of the microlead.

Note that this volume is formed only by the interstitial space 24 described above, and it is not a central lumen or other internal specific recess formed within the microlead. Indeed, as can be understood from reading the description above, given its very small diameter, the microlead does not contain a central lumen or other internal specific recess. This is unlike other types of leads which provide for the introduction of a guidewire in a central lumen, or the use of such a lumen, for example for the injection of a contrast medium. The inside of the microlead is on the contrary full and solid (except the interstitial spaces).

The basic idea of the invention is to use the interstitial space 24 to accommodate a charge of soluble pharmacologically active agent, which can be gradually released into the microlead environment via the exposed areas 16, by which the interstitial space 24 communicates with the surrounding outside environment.

Advantageously, this pharmacologically active agent is an anti-inflammatory agent, e.g. a glucocorticoid such as dexamethasone sodium phosphate (DSP hereinafter). This anti-inflammatory diffuses to the outside through the exposed zones 16 (as shown at 26 in FIG. 2). This provides for the anti-inflammatory agent to act precisely in the area 28 of the immediate environment of the microlead electrodes, wherein it is specifically required to reduce inflammation. Reducing inflammation helps to avoid over-consumption caused by raising the capture threshold, or any risk of loss of capture, as explained above.

DSP has the advantage of being a very hygroscopic and highly soluble material in water, allowing even with a very small volume, to have sufficient charge to get the desired efficiency for the required time. Thus, with the above value of a residual useful volume of 42.7 mm$^3$, one can load in this volume, for example, about 145 μg of DSP. This quantity is sufficient and nevertheless, less than the maximum regulatory limit of 1 mg. With a solution of 2.35 g of DSP for 100 ml of deionized water, however, it is possible to achieve the limit of 1 mg preload (for a microcable of 1 meter long) if it is necessary to increase the efficiency.

Once the lead is implanted, it will be in contact with the patient's blood. In this way, the DSP in solid form in the interstitial space 24 will rehydrate easily through the windows constituted by the exposed areas 16 because of the very high affinity of this agent for water. The DSP then dilutes in the blood by gradually leaving the exposed areas 16, thereby reducing the inflammation in the adjacent tissue. The concentration gradient between, on the one hand, the blood-circulating around the microlead and, on the other hand, the internal environment of the microlead, maintains the diffusion of the DSP to the outside of the lead.

Figure 4:
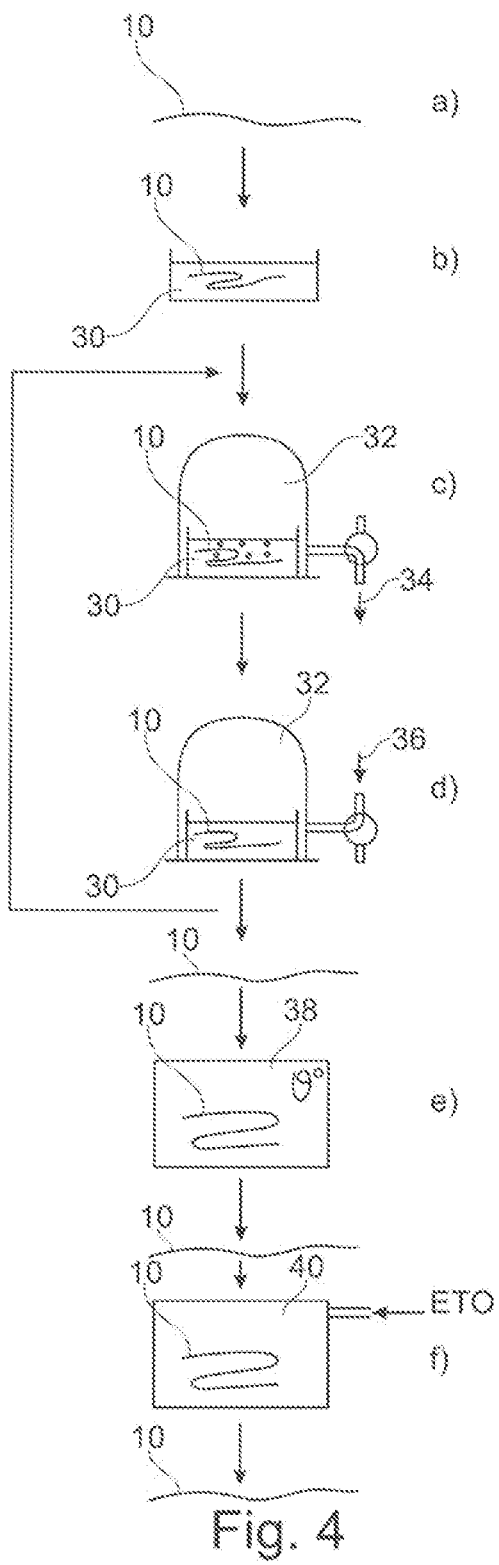
FIG. 4 shows the successive steps of the method of realization of the microlead of the invention.

FIG. 4 shows the successive steps of a method specially adapted for the manufacture of a lead such as the one that was just described. There is at the start (step a) a microlead 10 having the structure illustrated in FIGS. 1 to 3, provided after extrusion of the insulation layer 14 and the removal thereof at the location of the exposed zones 16, forming the electrodes.

The next step (step b) comprises immersing this microlead 10 in a bath 30 of a solution of the pharmacologically active agent to load the lead, for example, a solution of 0.3 g of DSP in 100 ml of deionized water. The lead is fully immersed in this solution 30 and maintained therein. Alternatively, an organic solution such as alcohol can also be used to accelerate the evaporation in the next step.

Subsequently (step c), the assembly is placed in a sealed chamber 32 connected to a vacuum pump 34 for emptying the chamber 32 of the air initially present, until stabilization of the depression. The air in the interstitial space of the lead 24 is then evacuated by the exposed zones 16 and rises to the surface of the liquid 30 in the form of bubbles visible by the operator. After stabilization, the pressure in the chamber 32 is recovered by the air intake 36 (step d), which has the effect of causing the penetration of the liquid solution 30 in the body of the microlead 10 in the interstitial space of the latter, replacing the void that had been formed in the previous step.

The cycle of steps c and d can be repeated several times to further improve the impregnation of the interstitial space 24 by the DSP solution. This c-d cycle (atmospheric pressure/vacuum/atmospheric pressure) can optionally be replaced or supplemented by a cycle of the type atmospheric pressure/vacuum/a few atmospheres overpressure/atmospheric pressure, which improves the rate of filling of the interstitial space 24 within the microlead (fewer residual bubbles) and/or accelerates the filling operation.

As an alternative to steps b-d, filling of the liquid steroid in the interstitial space of the microlead may be accomplished by injection with a syringe from an end of the sheathed microcable, sealingly coupled to the syringe for example by an adapter of the stuffing box type. The liquid may be injected until the appearance of a drop at the opposite end. This allows a filling under a pressure higher than 1 bar, in a more complete (less residual bubbles) and faster method. Note that in this case the step of filling the steroid can occur either after or before the cable sheathing, but before the ablation of the insulation layer to form the exposed areas (otherwise the steroid injected under pressure through one end would escape by these exposed zones before reaching the other end). Alternatively, in a preferred embodiment, filling the liquid occurs after ablation, but by temporarily masking the electrode windows by a retracted overtube removed after injection.

The lead 10 is then put in a chamber 38 to dry in an atmosphere as dry as possible (step e). For example, the lead may dry for four days between 20 and 40° C., in order to more completely extract the liquid phase of the DSP solution, the liquid phase which had served as a vehicle for the DSP. This drying causes recrystallization of the DSP into the interstitial space 24 of the microlead, wherein the DSP is then in the form of a dry soluble material. The lead can then be subjected to a sterilization cycle of conventional type (step f), for example by passage through a chamber 40 supplied with ethylene oxide ETO.

Figure 5:
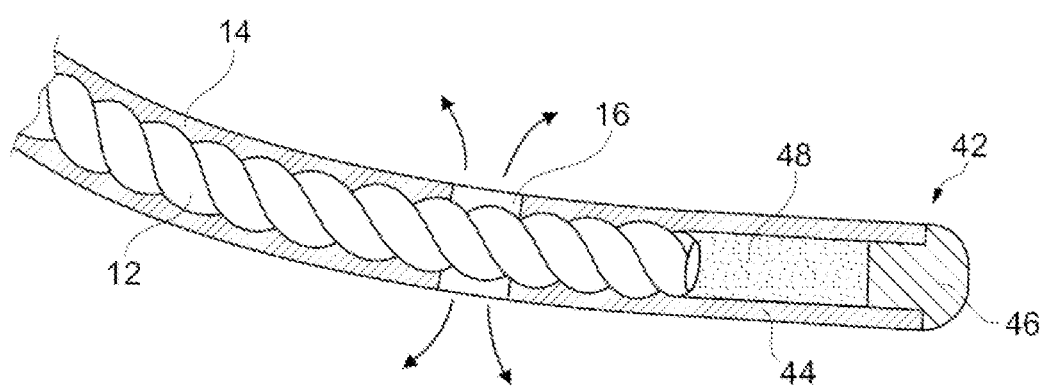
FIG. 5 is an enlarged view, in section, of the distal end of the microlead in an alternative embodiment thereof.

FIG. 5 is an enlarged view, in section, of the distal end 42 of the microlead. In the embodiment shown, the insulation layer 14 extends (at 44) beyond the termination of the microcable and to a plug (at 46) at the end thereof, creating a vacuum space 48 which can serve as a reservoir for steroid (originally in liquid form, then in powder after drying). In particular, the atraumatic distal portion of the lead can assume this tank function. In this way, advantageously, the electrodes 16 located at a few centimeters from the distal portion 42 of the microlead will have more steroid reserve to be released (reserve contained in the space 48) than the proximal electrodes, the reserves of which correspond to a few tens of centimeters of the microlead leading to the lead connector.

The invention claimed is:

1. A detection/stimulation microlead for implantation in venous, arterial or lymphatic networks and having an active distal portion devoid of a central lumen, the microlead comprising:
    an electrically conductive cable formed by a strand of microcables, each microcable being formed of a strand of individual metallic wires;
    an insulation layer of an electrically insulating material, sheathing the cable;
    a plurality of exposed areas formed in the insulation layer so as to form corresponding electrodes of the microlead;
    an interstitial space defined between the microcables and an internal wall of the insulation layer between the plurality of exposed areas; and
    a pharmacologically active agent present in the interstitial space and configured to gradually diffuse from the interstitial space into the plurality of exposed areas and into an environment of the microlead after implantation thereof.

2. The microlead of claim 1, wherein the pharmacologically active agent is soluble.

3. The microlead of claim 2, wherein the pharmacologically active agent is an anti-inflammatory agent.

4. The microlead of claim 3 wherein the anti-inflammatory agent is a glucocorticoid provided by dexamethasone sodium phosphate.

5. The microlead of claim 2, wherein the anti-inflammatory agent is a non-steroidal anti-inflammatory agent.

6. The microlead of claim 1, wherein a distal end of the microlead comprises an extension of the insulation layer beyond a termination of said cable, said extension defining a cavity forming an additional reservoir for the pharmacologically active agent, the reservoir being closed at its distal end by an atraumatic element.

7. The microlead of claim 1, wherein a diameter of the distal end of the microlead is less than 0.5 mm.

8. The microlead of claim 1, wherein the insulation layer comprises an ethylene tetrafluoroethylene layer.

9. The microlead of claim 1, wherein the insulation layer has a thickness of 25 μm.

10. The microlead of claim 1, wherein the interstitial space is approximately 50% of a volume delimited by the internal wall of the insulation layer.

11. A method for providing a pharmacologically active agent to a stimulation area in a venous, arterial, or lymphatic network, the method comprising:
    providing a microlead, the microlead comprising:
        an active distal portion formed by an electrically conductive cable formed by a strand of microcables, each microcable formed of a strand of individual metallic wires;
        an insulation layer of an electrically insulating material sheathing the cable;
        a plurality of exposed areas formed in the insulation layer so as to form corresponding electrodes of the microlead; and
        an interstitial space defined between the microcables and an internal wall of the insulation layer between the plurality of exposed areas;
    introducing a pharmacologically active agent to the interstitial space;
    implanting the microlead in the venous, arterial, or lymphatic network; and
    allowing the pharmacologically active agent to gradually diffuse from the interstitial space into the plurality of exposed areas and into tissue surrounding the at least one exposed area at the stimulation area.

12. The method of claim 11, wherein the pharmacologically active agent is an anti-inflammatory agent.

13. The method of claim 12, wherein the anti-inflammatory agent is a glucocorticoid.

14. The method of claim 13, wherein the glucocorticoid is dexamethasone sodium phosphate.

15. The method of claim 12, wherein the anti-inflammatory agent is a non-steroidal anti-inflammatory agent.

16. The method of claim 12, wherein the introducing comprises:
    introducing the pharmacologically active agent in an aqueous solution into the interstitial space; and
    allowing the solution to dry so as to allow recrystallization of the pharmacologically active agent into a solid form.

17. The method of claim 16, wherein allowing the pharmacologically active agent to gradually diffuse comprises:
    allowing the pharmacologically active agent to rehydrate by the plurality of exposed areas once the microlead is implanted; and
    allowing the pharmacologically active agent to form a concentration gradient between blood circulating around the microlead and an internal environment of the microlead.

18. The microlead of claim 1, wherein the interstitial space is also defined between the wires of each microcable, and wherein the pharmacologically active agent is also present in the interstitial space defined between the wires of each microcable.

19. The microlead of claim 1, wherein the pharmacologically active agent present in the interstitial space is introduced to the interstitial space by evacuating air of the interstitial space and causing the pharmacologically active agent to replace a void formed by the evacuation of the air of the interstitial space.

20. The method of claim 11, wherein the introducing comprises:
    evacuating air of the interstitial space; and
    causing the pharmacologically active agent to replace a void formed by the evacuation of the air of the interstitial space.

* * * * *